(12) United States Patent
Martin, Jr. et al.

(10) Patent No.: US 9,681,668 B2
(45) Date of Patent: Jun. 20, 2017

(54) **CONTROL OF PLANT DISEASES AND ENHANCING PLANT GROWTH USING A COMBINATION OF A *TRICHODERMA VIRENS* SPECIES AND A RHIZOSPHERE COMPETENT *TRICHODERMA HARZIANUM* SPECIES**

(71) Applicant: BioWorks, Inc., Victor, NY (US)

(72) Inventors: William Randolph Martin, Jr., Canandaigua, NY (US); Christopher Kent Hayes, Land O Lakes, FL (US)

(73) Assignee: BioWorks, Inc., Victor, NY (US)

( * ) Notice: Subject to any disclaimer, the term of this patent is extended or adjusted under 35 U.S.C. 154(b) by 324 days.

(21) Appl. No.: 14/610,104

(22) Filed: Jan. 30, 2015

(65) Prior Publication Data

US 2015/0148232 A1   May 28, 2015

Related U.S. Application Data

(63) Continuation of application No. 12/503,194, filed on Jul. 15, 2009, now abandoned.

(60) Provisional application No. 61/081,497, filed on Jul. 17, 2008.

(51) Int. Cl.
*A01N 63/04* (2006.01)
*A01N 65/00* (2009.01)
*C12N 1/14* (2006.01)

(52) U.S. Cl.
CPC ............ *A01N 65/00* (2013.01); *A01N 63/04* (2013.01); *C12N 1/14* (2013.01)

(58) Field of Classification Search
CPC ...................................................... A01N 63/04
See application file for complete search history.

(56) References Cited

U.S. PATENT DOCUMENTS

| | | | |
|---|---|---|---|
| 4,748,021 | A | 5/1988 | Chet et al. |
| 5,068,105 | A | 11/1991 | Lewis et al. |
| 5,165,928 | A | 11/1992 | Smith et al. |
| 5,194,258 | A | 3/1993 | Paau et al. |
| 5,260,212 | A | 11/1993 | Marugg et al. |
| 5,260,213 | A | 11/1993 | Harman et al. |
| 5,273,749 | A | 12/1993 | Bok et al. |
| 6,881,705 | B2 | 4/2005 | Garnier et al. |
| 6,939,831 | B1 | 9/2005 | Caminade et al. |
| 2002/0031504 | A1 | 3/2002 | Beudeker |
| 2002/0103083 | A1 | 8/2002 | Harman |
| 2003/0026797 | A1 | 2/2003 | Beudeker |
| 2004/0167144 | A1 | 8/2004 | Verbruggen et al. |
| 2004/0235874 | A1 | 11/2004 | Duvert et al. |
| 2005/0019420 | A1 | 1/2005 | Duvert |
| 2007/0060477 | A1 | 3/2007 | Pedersen et al. |

(Continued)

FOREIGN PATENT DOCUMENTS

| | | |
|---|---|---|
| EP | 0 387 640 A1 | 9/1990 |
| EP | 0 544 039 B1 | 6/1993 |

(Continued)

OTHER PUBLICATIONS

Declaration of Matthew S. Krause, Ph.D. under 37 C.F.R. § 1.132.

(Continued)

*Primary Examiner* — Rosanne Kosson
(74) *Attorney, Agent, or Firm* — LeClairRyan (57) ABSTRACT

The combination of a *Trichoderma virens* species and a rhizosphere competent *Trichoderma harzianum* species is used to control plant diseases and enhance plant growth.

16 Claims, 1 Drawing Sheet

(56) References Cited

U.S. PATENT DOCUMENTS

2008/0160101 A1 7/2008 Pujos et al.
2009/0308121 A1 12/2009 Reddy et al.

FOREIGN PATENT DOCUMENTS

| | | |
|---|---|---|
| EP | 1 279 335 A1 | 1/2003 |
| EP | 1 384 405 A1 | 1/2004 |
| EP | 1 427 288 B1 | 12/2004 |
| EP | 1 411 766 B1 | 3/2005 |
| EP | 1 543 723 A1 | 6/2005 |
| WO | 97/16974 A1 | 5/1997 |
| WO | 97/47202 A1 | 12/1997 |
| WO | 03/011030 A1 | 2/2003 |
| WO | 03/024228 A1 | 3/2003 |
| WO | 2005/058036 A1 | 6/2005 |
| WO | 2005/095579 A1 | 10/2005 |
| WO | 2006/089388 A1 | 8/2006 |
| WO | 2007/110686 A2 | 10/2007 |
| WO | 2008/029423 A1 | 3/2008 |
| WO | 2009/091557 | 7/2009 |

OTHER PUBLICATIONS

Examination Report for corresponding Canadian Patent Application No. 2,729,244 dated Oct. 26, 2015.
Translation of First Office Action for corresponding China Patent Application No. 200980136388.5 dated Nov. 28, 2012.
Translation of Second Office Action for corresponding China Patent Application No. 200980136388.5 dated Oct. 15, 2013.
Communication from European Patent Office for corresponding Application No. 09 790 472.6-1454 dated Jul. 7, 2014.
Translation of First Office Action for corresponding Mexico Patent Application No. MX/a/2011/00498 (Redacted) (Jun. 11, 2013).
Translation of Second Office Action for corresponding Mexico Patent Application No. MX/a/2011/00498 (Redacted) (Feb. 25, 2014).
Translation of Third Office Action for corresponding Mexico Patent Application No. MX/a/2011/00498 (Redacted) (Oct. 2, 2014).
Translation of First Office Action for corresponding divisional China Patent Application No. 201410269797.5 dated Dec. 31, 2015.
Translation of Second Office Action for corresponding divisional China Patent Application No. 201410269797.5 dated Oct. 18, 2016.
Smith et al., "Potential for Biological Control of Phytophthora Root and Crown Rots of Apple by *Trichoderma* and *Gliocladium* spp.," Phytopathology 80:880-885 (1990).
Costa et al., "Biological Control of Phytophthora Root Rot of Avocado With Microorganisms Grown in Organic Mulches," Brazilian J. Microbiol. 31:239-246 (2000).
Bacillus subtilis EMBL-EBI, http://web.archive.org/web/20071130185400/http://www.ebi.ac.uk/2can/genomes/bacteria/Bacillus_subtilis.html (Nov. 30, 2007).
Harman, "Development and Benefits of Rhizosphere Competent Fungi for Biological Control of Plant Pathogens," J. Plant Nutr. 15: 835-843 (1992).
Bailey & Lumsden, Direct Effects of Trichoderma and Gliocladium on Plant Growth and Resistance to Pathogens in Trichoderma & Gliocladium: vol. 2—Enzymes of Biological Control and Commercial Applications, Chapter 9 (Gary E. Harman & Christian P. Kubicek eds., Taylor and Francis 1998).
Sivan & Harman, "Improved Rhizosphere Competence in a Protoplast Fusion Progeny of Trichoderma harzianum," J. Gen. Microbial. 137:23-29 (1991).
Gams & Bissett, Morphology and Identification of Trichoderma, in Trichoderma and Gliocladium: vol. 1—Basic Biology, Taxonomy and Genetics (Christian P. Kubicek & Gary E. Harman eds., Taylor and Francis 1998).
Ahmad & Baker, "Rhizosphere Competence of Trichoderma harzianum," Phytopathology 77:182-189 (1987).
Elad & Chet, "Improved Selective Media for Isolation of *Trichoderma* spp. or *Fusarium* spp.," Phytoparasitica 11:55-58 (1983).
Papavizas & Lumsden, "Improved Medium for Isolation of *Trichoderma* spp. from Soil," Plant Disease 66:1019-1020 (1982).
Lewis et al., "A Formulation of Trichoderma and Gliocladium to Reduce Damping-Off Caused by Rhizoctonia solani and Saprophytic Growth of the Pathogen in Soilless Mix," Plant Dis. 82:501-506 (1998).
International Search Report and Written Opinion for PCT/US2009/050706 (mailed Dec. 23, 2010).
Inoculant Guide, American's Best Inoculants, ABM 127, Advanced Biological Marketing (2003).
The Effect of Inoculant Seed Treatment on Soybean Yield (2003). Advanced Biological Marketing (2002).
Damicone, J., "Snap Bean Pod Decay," (2004).
Damicone et al., "Spinach Seed Treatment," (2004).
Damicone et al., "Spinach White Rust Fall," (2004).
Damicone et al., "Spinach White Rust Spring," (2004).
Damicone, J., "Watermelon Anthracnose," (2004).
Material Safety Data Sheet, ABM 127 (2002).
Lorito et al., "Potential of Genes and Gene Products from *Trichoderma* sp. and *Gliocladium* sp. for the Development of Biological Pesticides," Molecular Biology 2:209-17 (1994).
Lynch et al., "Prospects for Control of Pythium Damping-Off of Lettuce with *Trichoderma, Gliocladium*, and *Enterobacter* spp.," Biol. Fertil. Soils 12:95-9 (1991).
Nutri-Life Trichoshield, "Beneficial Fungi to Improve the Balance Between Desired and Undesirable Micro-organisms on the Leaf Surface and in the Soil," Nutri-Tech Solutions pp. I-2 (2007).
Papavizas et al., "Effect of Gliocladium and Trichoderma on Damping-Off and Blight of Snapbean Caused by Sclerotium Rolfsii in the Greenhouse," Plant Pathology 38:277-86 (1989).
Raj et aL, "Synergistic Effects of Trichoshield on Enhancement of Growth and Resistance to Downy Mildew in Pearl Millet," BioControl 50:493-509 (2005).
Samuels, "Trichoderma: A Review of Biology and Systematics of the Genus," Mycol. Res. 100(8):923-35 (1996).
Shin et al., "Molecular Characterization of Intergeneric Hybrids Between Trichoderma Harzianum and Gliocladium Virens," Journal of Microbiology and Biotechnology 7(3):161-6 (1997).
Yigit et al., "Control of Fusarium Wilt of Tomato by Combination of Fluorescent Pseudomonas, Non-pathogen Fusarium and Trichoderma Harzianum T-22 in Greenhouse Conditions," Plant Pathology Journal 6(2):159-63 (2007).
Examination Report for corresponding Canadian Patent Application No. 2,729,244 dated Nov. 25, 2016.

Population of T22 vs. G41 in the Rhizosphere of Corn

CONTROL OF PLANT DISEASES AND ENHANCING PLANT GROWTH USING A COMBINATION OF A *TRICHODERMA VIRENS* SPECIES AND A RHIZOSPHERE COMPETENT *TRICHODERMA HARZIANUM* SPECIES

This application is a continuation of U.S. patent application Ser. No. 12/503,194, filed Jul. 15, 2009, which claims benefit of U.S. Provisional Patent Application Ser. No. 61/081,497, filed Jul. 17, 2008, which is hereby incorporated by reference in its entirety.

FIELD OF THE INVENTION

The present invention relates to the control of plant diseases and enhancing plant growth using a combination of a rhizosphere competent *Trichoderma harzianum* species and a *Trichoderma virens* species.

BACKGROUND OF THE INVENTION

*Phytophthora* spp are pathogenic agents from the family of Pythiaceae known to be involved in various plant diseases. Sudden oak death, soybean root rot, apple crown and collar rot, root rot, affecting American chestnuts, rhododendron, African violet, or strawberries, are just examples of diseases caused by this group of pathogens. Typically, plant diseases caused by *Phytophthora* are considerably difficult to control and often lead to the death of the plant. This pathogen is a widespread and an economic problem to growers around the world. For example, *Phytophthora infestans* was the infective agent of the potato that caused the Great Irish Famine between 1845 and 1849. Presently, in North America growers are still facing the ravage of this pathogenic agent. Many conventional management techniques such as rootstock selection and site modification to control *Phytophthora* spp have been mostly unreliable.

Crown and collar rot, caused by at least four *Phytophthora* spp. (Jeffers et al., *Phytopathology* 2:533-538 (1982)) is a widespread and economically serious problem of apples throughout the Northeast U.S. In New York State, this disease appears to be the most common biological cause of premature tree decline and death, and, in Pennsylvania, many growers have abandoned the horticulturally-desirable MM 106 rootstock because of high crown rot incidence or its perceived threat. Stem and root rot of soybeans caused by *Phytophthora sojae* Kaufmann and Gerdemann (also denoted *Phytophthora megasperma* forma specialis *glycinea*) is also a widespread and serious problem. Because no single approach to the control of *Phytophthora* crown rot has proved reliable, growers have been advised to adopt an integrated or additive disease management strategy, utilizing a combination of site selection, site modification, rootstock selection, and chemical treatments where appropriate.

*Pythium*, like others in the family Pythiaceae, are usually characterized by their production of coenocytic hyphae, hyphae without septations. These are commonly called water molds. *Pythium* damping off is a very common problem in fields and greenhouses, where the organism kills newly emerged seedlings. This disease complex usually involves other pathogens such as *Phytophthora* and *Rhizoctonia*. *Pythium* wilt is caused by zoospore infection of older plants leading to biotrophic infections that become necrotrophic in response to colonization/reinfection pressures or environmental stress, leading to minor or severe wilting caused by impeded root functioning. See Jarvis, W. R., "Managing Diseases in Greenhouse Crops," APS Press, St. Paul, Minn. (1992); Bagnall, R., "Control of *Pythium* Wilt and Root Rot of Hydroponically Grown Lettuce by Means of Chemical Treatment of the Nutrient Solution," M. Sc Thesis, University of Pretoria, Pretoria, South Africa (2007); Plaats-Niterink A J van der, "Monograph of the Genus *Pythium*," *Studies in Mycology* 21:1-242 (1981); Levesque et al., "Molecular Phylogeny and Taxonomy of the Genus *Pythium*," *Mycological Research* 108:1363-1383 (2004); Jarvis, W. R., "Managing Diseases in Greenhouse Crops," APS Press, St. Paul, Minn. (1992); Owen-Going, T. N., "Etiology and Epidemiology of *Pythium* Root Rot in Bell Pepper (*Capsicum annuum* L.) in Commercial-Scale and Small-Scale Hydroponic Systems," M.Sc. thesis, University of Guelph, Guelph, Ontario (2002); Owen-Going et al., "Relationships of *Pythium* Isolates and Sweet Pepper Plants in Single-Plant Hydroponic Units," *Canadian Journal of Plant Pathology* 25:155-167 (2003); Owen-Going, T. N., "Quantitative Investigations of Phenolic Compounds Associated With Root Rot of Hydroponic Pepper (*Capsicum annuum* L. Caused by *Pythium aphanidermatum*, (Edson) Fitzp. Ph.D. Thesis, University of Guelph, Guelph, Ontario (2005).

Many *Pythium* species, along with their close relatives, *Phytophthora* species are plant pathogens of economic importance in agriculture. *Pythium* spp. tend to be very generalistic and unspecific in their host range. They infect a large range of hosts, while *Phytophthora* spp. are generally more host-specific. For this reason, *Pythium* spp. are more devastating in the root rot they cause in crops, because crop rotation alone will often not eradicate the pathogen (nor will fallowing the field, as *Pythium* spp. are also good saprotrophs, and will survive for a long time on decaying plant matter).

*Fusarium* is a large genus of filamentous fungi widely distributed in soil and in association with plants. Most species are harmless saprophytes and are relatively abundant members of the soil microbial community. Some species produce mycotoxins in cereal crops that can affect human and animal health if they enter the food chain. The main toxins produced by these *Fusarium* species are fumonisins and trichothecenes. The genus includes a number of economically important plant pathogenic species. See Priest and Campbell, "Brewing Microbiology," 3rd edition., ISBN 0-306-47288-0; Walsh et al., "Spectrum of Mycoses," *In: Baron's Medical Microbiology* (Baron S et al, eds.), 4th ed., Univ of Texas Medical Branch. (via NCBI Bookshelf) ISBN 0-9631172-1-1 (1996); Howard, D H, "Pathogenic Fungi in Humans and Animals," 2nd ed., Marcel Dekker. (via Google Books) ISBN 0-8247-0683-8 (2003); Van der Walta et al., "*Fusarium* Populations in the Household Food Gardens of a Peri-Urban Community," *South African Journal of Science* 103 (2007); World Health Organization (1999-09-01), "Toxic Effects of Mycotoxins in Humans" (2007); Drug Policy Alliance, "Repeating Mistakes of the Past: Another Mycoherbicide Research Bill," (2006); Yellow rain: Thai bees' Faeces Found. *Nature* PMID 6709055 (1984); Imamura et al., "*Fusarium* and *Candida Albicans* Biofilms on Soft Contact Lenses: Model Development, Influence of Lens Type, and Susceptibility to Lens Care Solutions," *Antimicrob. Agents Chemother.* 52(1):171-182 (2008).

*Fusarium graminearum* commonly infects barley if there is rain late in the season. It is of economic impact to the malting and brewing industries as well as feed barley. *Fusarium* contamination in barley can result in head blight and in extreme contaminations the barley can appear pink. The genome of this wheat and maize pathogen has been sequenced. *Fusarium graminearum* can also cause root rot and seedling blight. The total losses in the US of barley and wheat crops between 1991 and 1996 have been estimated at $3 billion.

*Rhizoctonia* spp. are among the most diverse of plant pathogens, causing root, stem and foliar diseases of many of our most important herbaceous and woody ornamentals. *Rhizoctonia* spp. usually attack plants at the soil line, causing root loss and constriction of the stem which results in girdling and death of the tops. This pathogen can attack leaves as well and is especially severe when plants are grown close together and kept moist. Entire stock beds or flats can be lost to *Rhizoctonia* in very short periods of time. The pathogen is soil-borne which means it lives in the soil or potting medium. It causes both pre- and post-emergence damping-off of many ornamental crops such as Vinca, Impatiens, stock, and snapdragon (Chase, A. R., "*Rhizoctonia* Diseases on Ornamentals," *Western Connection, Turf and Ornamentals* (1998)).

*Thielaviopsis basicola* (Berk. & Br.) Ferraris is a soil inhabitant that attacks more than 100 plant species in 33 families. Members of the Fabaceae, Solanaceae, and Cucurbitaceae families are especially affected by *T. basicola* (Shew et al., Eds., "Compendium of Tobacco Diseases,". St. Paul, Minn.: APS Press, pp. 28-29 (1991)). The common name 'black root rot' is based on darkly pigmented chlamydospores that form in the root cells of hosts and giving a 'blackened' appearance to the root tip (Alexopoulos et al., "Introductory Mycology," 4th Ed., pp. 869 (1996)). The black root rot fungus is a member of the Hyphomycetes, order Moniliales, family Dematicaceae (Shew et al., Eds., "Compendium of Tobacco Diseases,". St. Paul, Minn.: APS Press, pp. 28-29 (1991)). General symptoms are root rot and branch dieback. *Thielaviopsis basicola* can be found in all regions of the world, especially in regions with cool climates. Black root rot can affect a wide range of woody and herbaceous plants including tobacco, holly, begonia, geranium, poinsettia, and pansy (Agrios, G. N., "Plant Pathology," 4th ed., p. 358 (1997); Alexopoulos et al., "Introductory Mycology," 4th Ed., pp. 869 (1996); Daughtrey et al., "Compendium of Flowering Potted Plants," pp. 90 (1995); Lambe et al., "Diseases of Woody Ornamental Plants and Their Control in Nurseries," pp. 130 (1986); Shew et al., Eds., "Compendium of Tobacco Diseases," pp. 28-29 (1991)).

*Sclerotium rolfsii*, an omnivorous, soilborne fungal pathogen, causes disease on a wide range of agricultural and horticultural crops. Although no worldwide compilation of host genera has been published, over 270 host genera have been reported in the United States alone. Susceptible agricultural hosts include sweet potato (*Ipomea batatas*), pumpkin (*Cucurbita pepo* L.), corn (*Zea mays*), wheat (*Triticum vulgare*) and peanut (*Arachis hypogea*). Horticultural crops affected by the fungus are included in the genera Narcissus, Iris, Lilium, Zinnia, and Chrysanthemum. See Aycock, R., "Stem Rot and Other Diseases Caused by *Sclerotium rolfsii*," *N.C. Agr. Expt. St. Tech. Bul.*, No. 174 (1966); Garren, K. H., "The Stem Rot of Peanuts and its Control," *Virginia Agr. Exp. Sta. Bull.* 144 (1959); Paolo, M. A., "A *Sclerotium* Seed Rot and Seedling Stem Rot of Mango," *Philippine Journal of Science* 52:237-261 (1933); Punja, Z. K., "The Biology, Ecology, and Control of *Sclerotium rolfsii*," *Annual Review of Phytopathology* 23:97-127 (1985); Takahashi, T., "A *Sclerotium* Disease of Larkspur," *Phytopathology* 17:239-245 (1927); Townsend et al., "The Development of Sclerotia of Certain Fungi," *Ann. Bot.* 21:153-166 (1954); Weber, G. F., "Blight of Carrots Caused by *Sclerotium rolfsii*, With Geographic Distribution and Host Range of the Fungus," *Phytopathology* 21:1129-1140 (1931); Zitter et al., "Compendium of Cucurbit Diseases," *Amer. Phytopath. Soc.*, St. Paul, Minn. (1966).

Although *S. rolfsii* is thought to have caused serious crop losses over many centuries, the first unmistakable report of the fungus dates back to 1892 with Peter Henry Rolfs' discovery of the organism in association with tomato blight in Florida. Since Rolfs' report in the late 19th century, the over 2,000 publications on the pathogen support evidence of its worldwide distribution, particularly in tropical and subtropical regions.

The wide host range, prolific growth, and ability to produce sclerotia contribute to the largest economic losses associated with the pathogen. From a global perspective, and local perspective for North Carolina, peanut crops sustain higher losses than any other agricultural crop. In 1959, the United States Department of Agriculture estimated losses from $10 million to $20 million associated with *S. rolfsii* in the southern peanut-growing region, with yield depletions ranging from 1-60% in fields in the NC coastal plains region.

There exists correlative evidence that certain *Trichoderma* spp. may be involved in the biological control of several diseases caused by *Phytophthora* spp., e.g., *T. viride* versus heart rot of pineapple caused by *P. parasitica* (Papazivas, *Ann. Rev. Phytopathol.* 23:23-54 (1985)). More compelling correlative evidence is supplied by the well-documented ability of composted hardwood bark (CHB) to provide control of *Phytophthora* disease of woody plants when incorporated into their rhizosphere (Hoitink et al., *Ann. Rev. Phytopathol.* 24:93-114 (1986)), including control of crown rot of apple under field conditions (Ellis et al., *Plant Dis.* 70:24-26 (1986)), and the related documentation that the addition of CHB to a container potting mix resulted in a 100 to 100,000 fold increase in the population levels of *T. harzianum* in this rooting medium (Nelson et al., *Phytopathology* 3:1457-1462 (1983)).

Biological control (biocontrol) of plant pathogens is increasingly becoming an essential component in plant disease management. Over-reliance on chemical pesticides, non-sustainable agricultural systems, poor site selection, and resource limitations are examples of agricultural problems faced by growers. Biocontrol offers an alternative to these recurrent/persistent problems in agriculture. Therefore, much emphasis is being placed on the application of such techniques in agriculture.

Many fungi and other microorganisms are known to control various plant pathogens. These biocontrol agents are particularly attractive, because they may be able to protect and colonize plant portions that are particularly inaccessible to conventional agricultural treatments (Harman et al., *Seed Sci. and Technol.* 11:893-906 (1983)). *Trichoderma* spp, a filamentous genus of fungi, have been shown to provide varying level of biological control to soil-borne plant pathogens. Five species of *Trichoderma* are known to be most important for biocontrol. They are *T. hamatum*, *T. harzianum*, *T. konigii*, *T. polysporum*, and *T. viride*. Desirable and essential traits for biocontrol capability are attributed to specific strains and not the species. For example, strains of *T. harzianum* have been involved in the treatment of cucumber. While there have been many advances in the use of *Trichoderma* as a biocontrol agent, it was not until 1992 that this fungus was reported in the treatment of diseases caused by soil-borne *Phytophthora* spp (Papavizas, *Ann. Rev. Phytopathol.* 23:23-54 (1985)). Three strains of *Gliocladium virens* (031, 035, and 041), now known as *Trichoderma virens*, have been used as biological agents (U.S. Pat. No. 5,165,928 to Smith et al.) to control plant diseases incited by *Phytophthora* spp, such as root rot, crown, and collar rot (Jeffers et al., *Phytopathology* 2:533-538 (1982)). However, this invention was limited to the treatment of plant diseases caused by *Phytophthora sojae*. Additionally, there is the strain GL-21 which is described in U.S. Pat. No. 5,068,105 to Lewis et al. and sold as SoilGard™.

Combinations of different biocontrol agents have been used to control disease. For example, Lewis et al., "A Formulation of *Trichoderma* and *Gliocladium* to Reduce Damping-off Caused by *Rhizoctonia solani* and Saprophytic Growth of the Pathogen in Soilless Mix," *Plant Disease*

82:501-06 (1998) uses a formulation of *Gliocladium virens* TRI-4 and *Trichoderma hamatum* GL-3, GL-21, or GL-32 for biocontrol. A talc-based formulation known as NUTRI-LIFE TRICHOSHIELD™ has been sold by Nutri-Tech Solutions Pty Ltd. as a plant root growth promoter. This formulation contains a mixture of beneficial fungal species, including *Trichoderma harzianum, Trichoderma lignorum,* and *Gliocladium virens* (now *Trichoderma virens*) together with bio-balancing *Bacillus subtilis*. Papavizas, et. al., "Effect of *Gliocladium* and *Trichoderma* on Damping-off and Blight of Snapbean Caused by *Sclerotium rolfsii* in the Greenhouse," *Plant Pathology* 38: 277-86 (1989) describes the use of 285 wild-type strains and mutants of *Gliocladium virens, Trichoderma hamatum, Trichoderma harzianum,* and *Trichoderma viride* against *Scelerotium rolfisii* in the greenhouse. Ten strains of *Gliocladium virens* and four strains of *Trichoderma harzianum* suppressed damping-off of snapbeans by 30-50% and blight by 36-74%. Single strains were as effective as or more effective than mixtures of strains. For instance, the mixture of G1-3 and Th-84 at $3\times10^5$ conidia per g soil from each strain was less effective than G1-3 or Th-84 used alone and the triple mixture was least effective. These results suggest to those skilled in the art that *Trichoderma harzianum* and *Gliocladium virens* should be used separately to treat plants rather than doing so in combination. In any event, none of the above-described combinations of biocontrol agents involve utilization of a rhizosphere competent *Trichoderma harzianum* species.

The present invention is directed to overcoming these and other deficiencies in the art.

SUMMARY OF THE INVENTION

One aspect of the present invention relates to a biocontrol composition comprising a rhizosphere competent *Trichoderma harzianum* species and a *Trichoderma virens* species.

Another aspect of the present invention relates to a method of controlling plant diseases mediated by *Phytophthora, Pythium, Fusarium, Rhizoctonia, Sclerotium,* and/or *Thielaviopsis* species. The method includes providing a rhizosphere competent *Trichoderma harzianum* species and providing a *Trichoderma virens* species. The *Trichoderma harzianum* species and *T. virens* species are applied to plants under conditions effective to treat plant disease mediated by *Phytophthora, Pythium, Fusarium, Rhizoctonia, Sclerotium,* and/or *Thielaviopsis* species.

Another aspect of the present invention relates to a method of enhancing plant growth. This involves providing a rhizosphere competent *Trichoderma harzianum* species and providing a *Trichoderma virens* species. The rhizosphere competent *Trichoderma harzianum* species and the *Trichoderma virens* species are applied to plants under conditions effective to enhance plant growth.

Because of multiple shortcomings observed with individual or specific biocontrol agents, there is much need for a diverse agent capable of treating various *Phytophthora* spp. This will not only increase productivity of the targeted plants, but will also potentially lower the buying cost of having to use multiple biocontrol agents.

The combination of rhizosphere competent *T. harzianum* and *T. virens* prevents plants from becoming diseased and performs better than either organism alone; there is an enhanced effect on disease protection when the two are combined. Further, the combination performed as well as chemical fungicides. In particular, plants treated with this combination showed no symptoms or less severe symptoms of pathogen infection and had greater root mass, grew taller, and were more marketable than plants treated with either biological agent alone. Diseased plants typically exhibit multiple symptoms, generally associated with lack of root growth, and eventually, root death.

Growers and consumers are interested in reducing the use of chemical pesticides in agricultural crops and seek alternative materials for pest management. Effective biological control materials that have a low impact on the environment and non-target organisms can be used as alternatives to, or in a program along with, traditional chemical pesticides. The present invention provides a broad-spectrum control of multiple diseases in agronomic crops and a safe alternative to chemical pesticides.

DETAILED DESCRIPTION OF THE INVENTION

One aspect of the present invention relates to a biocontrol composition comprising a rhizosphere competent *Trichoderma harzianum* species and a *Trichoderma virens* species.

In one embodiment of the present invention, the biocontrol composition includes the *Trichoderma virens* species G41, formerly known as *Gliocladium virens*, (ATCC Accession No. 20906) and the rhizosphere competent *Trichoderma harzianum* species T22 (ATCC Accession No. 20847). T22 is fully discussed in U.S. Pat. No. 5,260,213 to Harman et al., which is hereby incorporated by reference in its entirety. G41 is fully described in U.S. Pat. No. 5,165,928 to Smith et al., which is hereby incorporated by reference in its entirety.

The rhizosphere is the narrow region of soil that is directly influenced by root secretions and associated soil microorganisms. It is teeming with bacteria that feed on sloughed-off plant cells, termed rhizodeposition, and the proteins and sugars released by roots. The protozoa and nematodes that graze on bacteria are also concentrated near roots. Thus, much of the nutrient cycling and disease suppression needed by plants occurs immediately adjacent to roots. The rhizoplane is the external surface of roots and of the soil particles and debris adhering to them. "Rhizosphere competency" is a measure of the ability of a microorganism to colonize the rhizosphere.

Specific to biological control agents, rhizosphere competent organisms have the physiological and genetic ability to proliferate along the root as it develops. This ability is distinctly different from organisms capable of colonizing only specific points along the root (Harman, *J. Plant Nutr.* 15:835-843 (1992), which is hereby incorporated by reference in its entirety). *Trichoderma* spp. are one of the few fungal biocontrol agents in which rhizosphere competence has been demonstrated. In fact, most strains of *Trichoderma* are not rhizosphere competent (Bailey et al., *Trichoderma and Gliocladium,* pp. 185-204 (1998), which is hereby incorporated by reference in its entirety). One important characteristic of *T harzianum* strain T22 is its rhizosphere competency (Sivan et al., "Improved Rhizosphere Competence in a Protoplast Fusion Progeny of *Trichoderma harzianum,*" *J. Gen. Microbiol.* 137:23-29 (1991), which is hereby incorporated by reference by its entirety).

The present invention can include a carrier. Suitable carriers include water, aqueous solution, slurries, granules, or powders.

Other additives suitable for inclusion in the composition are fertilizer, insecticide, fungicide, nematicide, or mixtures thereof.

Another aspect of the present invention relates to a method of controlling plant diseases mediated by *Phytophthora, Pythium, Fusarium, Rhizoctonia, Sclerotium* and/or *Thielaviopsis* species. The method includes providing a rhizosphere competent *Trichoderma harzianum* species and providing a *Trichoderma virens* species. The *Trichoderma harzianum* species and *T virens* species are applied to plants under conditions effective to treat plant disease mediated by *Phytophthora, Pythium, Fusarium, Rhizoctonia, Sclerotium,* and/or *Thielaviopsis* species.

Plant diseases mediated by *Phytophthora* species, which are treatable in accordance with the present invention, can result from *Phytophthora cactorum, Phytophthora cinnamomi, Phytophthora citricola, Phytophthora citrophthora, Phytophthora cryptogea, Phytophthora drecshsleri, Phytophthora infestans* and/or *Phytophthora nicotianae* infection.

Plant diseases mediated by *Pythium* species can result from infection by *Pythium aphanidermatum, Pythium irregulare,* and/or *Pythium ultimum.*

Plant diseases mediated by *Rhizoctonia* species can result from *Rhizoctonia solani* infection.

Plant diseases mediated by *Thielaviopsis* species can result from *Thielaviopsis basicola* infection.

Plant diseases caused by *Fusarium* species can be caused by *Fusarium oxysporum* species and related sub-species.

Plant diseases resulting from *Sclerotium* species can be mediated by *Sclerotium rolfsii*.

Plants treated in accordance with the present invention include agronomic row or other field crops: buckwheat, beans (soybean, snap, dry), corn (grain, seed, sweet corn, silage, popcorn, high oil), cotton, canola, peas (dry, succulent), peanuts, safflower, sunflower, alfalfa hay, forage crops (alfalfa, clover, vetch, and trefoil), berries and small fruits (blackberries, blueberries, currants, elderberries, gooseberries, huckleberries, loganberries, raspberries, strawberries, and grapes), bulb crops (garlic, leeks, onions, shallots, and ornamental bulbs), citrus fruits (citrus hybrids, grapefruit, kumquat, lines, oranges, and pummelos), cucurbit vegetables (cucumbers, melons, gourds, pumpkins, and squash), flowers, bedding plants, ornamentals, fruiting vegetables (eggplant, sweet and hot peppers, tomatillos, and tomatoes), herbs, spices, mints, hydroponic crops (cucumbers, tomatoes, lettuce, herbs, and spices), leafy vegetables and cole crops (arugula, celery, chervil, endive, fennel, lettuce (head and leaf), parsley, radicchio, rhubarb, spinach, Swiss chard, broccoli, Brussels sprouts, cabbage, cauliflower, collards, kale, kohlrabi, and mustard greens), asparagus, legume vegetable and field crops (snap and dry beans, lentils, succulent and dry peas, and peanuts), pome fruit (pears and quince), root crops (beets, sugarbeets, red beets, carrots, celeriac, chicory, horseradish, parsnip, radish rutabaga, salsify, and turnips), deciduous trees (maple and oak), pine, small grains (rye, wheat, sorghum, millet, stone fruits (apricots, cherries, nectarines, peaches, plums, and prunes), tree nuts (almonds, beech nuts, Brazil nuts, butternuts, cashews, chestnuts, filberts, hickory nuts, macadamia nuts, pecans, pistachios, and walnuts), tuber crops (potatoes, sweet potatoes, yams, artichoke, cassava, and ginger), and turfgrass (turf, sports fields, parks, established and new preparation of golf course tees, greens, fairways and roughs, seed production and sod production).

To control target pathogens, plants must be cultivated within the effective area of the biocontrol agent. Seeds can be planted in soil mixed with biocontrol agents. Several other methods of introducing the biocontrol to the plant would be equally effective. For example, the biocontrol agent could be fermented, formulated, or packaged. Then the biocontrol agent can be applied to the plant seed by dry or wet formulation and application to the seed. Alternatively, the biocontrol could be produced in an in-furrow formulation, wet or dry, which can be applied to the soil where the plant is to be grown. The biocontrol agent can even be applied as a spray, directed either in furrow during planting or to the soil surface after planting. The agent may also be applied as a drench to potted plants and may be incorporated into a growing medium. What is required is that the biocontrol agent be placed by some means in the soil environment adjacent to the growing plant. By "target pathogen" is meant the pathogen or pathogens, known or unknown, which threatens the crop plant.

Another aspect of the present invention relates to a method of enhancing plant growth. This involves providing a rhizosphere competent *Trichoderma harzianum* species and providing a *Trichoderma virens* species. The rhizosphere competent *Trichoderma harzianum* species and the *Trichoderma virens* species are applied to plants under conditions effective to enhance plant growth.

This aspect of the present invention is carried out with substantially the same materials and procedures described above with reference to the method of controlling diseases. It is directed to affecting any form of plant growth enhancement or promotion. This can occur as early as when plant growth begins from seeds or later in the life of a plant. For example, plant growth according to the present invention encompasses greater yield, increased quantity of seeds produced, increased percentage of seeds germinated, increased plant size, greater biomass, more and bigger fruit, earlier fruit coloration, and earlier fruit and plant maturation. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land. It is thus apparent that the present invention constitutes a significant advance in agricultural efficiency.

EXAMPLES

The examples that follow are given for illustrative purposes and are not meant to limit the invention described herein. These examples are given to demonstrate the synergy observed when a rhizosphere competent strain of *Trichoderma harzianum* (in this case, strain T22) is used together with *Trichoderma virens* (in this case, strain G41). This synergy is manifested as a marked increase in the control of plant disease, caused by a broad variety of pathogens. Finally, an example is given to show the significance of rhizosphere competence in the interaction, and how it affects the synergy between the *Trichoderma* strains.

Microbial strains were maintained as follows:
T22: maintained on silica gels in laboratory freezer, and grown out onto PDA plates as needed. Plates were used to inoculate a growing medium and allowed to incubate for a 2-week period. Spores were harvested via sieve after incubation and used to formulate a wettable powder.
G41: maintained on silica gels in laboratory freezer, and grown out onto PDA plates as needed. Plates were used to inoculate sterile rice and allowed to incubate for a 2-week period. Spores were harvested via sieve after incubation and used to formulate a wettable powder.

G21: Isolated from a commercially available product and grown out onto PDA plates as needed. Plates were used to inoculate sterile rice and allowed to incubate for a 2-week period. Spores were harvested via sieve after incubation and used to formulate a wettable powder.

T12: maintained on silica gels in laboratory freezer, and grown out onto PDA plates as needed. Plates were used to inoculate sterile rice and allowed to incubate for a 2-week period. Spores were harvested via sieve after incubation and used to formulate a wettable powder.

Plant pathogens: maintained on PDA agar plates at 30° C.

*Trichoderma* spores were formulated with a wettable carrier that contained at least $10^7$ colony-forming units per gram. Plants were treated with the formulated material in water at a concentration of 4 or 8 oz/100 gal.

Example 1—Treatment of Boxwoods Infected with *P. cinnamomi*

This example gives an illustration of the efficacy and synergy of a composition according to the present invention for controlling *Phytophthora cinnamomi* on boxwood plants.

Boxwoods, *Buxus microphylla asiaticum*, var. 'Winter Gem' were subjected to the soil drench treatments set forth in Table 1. Except for the non-inoculated controls, each plant was treated with *P. cinnamomi* inoculum to induce disease. Boxwood plants were obtained from a local nursery and placed into a 6 inch diameter pot containing pine bark: peat (3:1 volume:volume) potting media. The medium was amended with 14 lb of 17-7-12 Osmocote fertilizer per cubic yard of mix.

Inoculum of *P. cinnamomi* was grown on sterilized rice grains for 14 days at 24-26° C. prior to inoculation. To treat the plants with the pathogen inoculum, four holes were punched equidistant around the root ball, and four colonized rice grains were inserted in each hole. Each of the test materials was applied at the specified rate to the soil surface, using a 2.5 pint hand held sprayer. The chemical standard, mefenoxam (Subdue®), was applied to the soil surface 24 hours after the plant roots were inoculated with *P. cinnamomi* inoculum. T22 and G41 were applied to the soil surface 72 hours prior to root inoculation with *P. cinnamomi*.

A marketability rating was determined for each plant at one day after inoculation (DAI) with *P. cinnamomi,* 22 days DAI, and 54 days DAI. Using the following scale, each plant was rated by three researchers and the mean value was determined for each plant:

1: Dead plants
2: Poor, unsalable (severe chlorosis and poor top growth)
3: Moderate, salable (slight chlorosis and/or stunting; plant growth between 2 and 4)
4: Salable (few individual leaves with chlorosis, green foliage; plant growth between 3 and 5)
5: Excellent health, salable (no chlorosis; optimum top growth)

At 1, 22, and 54 DAI, plant height was measured from the crown to the highest point of the plant. Dry root weight and fresh shoot weight were determined at 22 and 54 DAI.

At 22 DAI, a subset of plants from each treatment were removed and examined. Plants were removed from the pots, and excess soil was carefully brushed from the roots. Above ground portions (shoots) were cut away from the below ground portions and dried in an oven. Dry root weights and fresh shoot weights were recorded. At 54 DAI, the experiment was terminated; the remaining plants were treated as above to determine dry root and shoot weights. Data were subjected to analysis of variance and treatment means were separated by Student-Newman-Keuls test at P=0.05.

TABLE 1

| Treatment | Rate |
|---|---|
| 1. Non-Inoculated Control | — |
| 2. Inoculated Control | — |
| 3. T22 (*Trichoderma harzianum*) | 4 oz/100 gal |
| 4. G41 (*Trichoderma virens*) | 8 oz/100 gal |
| 5. T22 + G41 | 4 oz + 8 oz/100 gal |
| 6. Mefenoxam | 1 oz/100 gal |

Marketability results are set forth in Table 2 which shows that plants treated with the combined T22 and G41 biocontrol agents were protected from developing disease symptoms, particularly compared to plants treated with a single organism separately.

TABLE 2

| | | Marketability: 1(dead)-5(excellent) Scale | | |
|---|---|---|---|---|
| Treatment | Rate | 5/26 | 6/21 | 7/10 |
| Non-inoculated control | — | 5 a | 4.3 a | 4.7 a |
| Inoculated control | — | 5 a | 2.1 d | 2.0 d |
| T22 | 4 oz/100 gal | 5 a | 3.6 bc | 3.6 bc |
| G41 | 8 oz/100 gal | 5 a | 3.4 c | 3.4 c |
| T22 + G41 | 4 oz/100 gal + 8 oz/100 gal | 5 a | 4.4 a | 4.5 a |
| Mefenoxam | 1 oz/100 gal | 5 a | 4.4 a | 4.7 a |
| LSD (P = 0.05) | | 0.0 | 0.51 | 0.54 |
| Standard Deviation | | 0.0 | 0.57 | 0.60 |
| CV | | 0.0 | 15.18 | 15.34 |

Mean values followed by different letters are significantly different (P = 0.05, Student-Newman-Keuls). Each value is a mean of 10 replicates.

Plants height results are shown in Table 3 with boxwoods subjected to combined treatment of T22 and G41 being substantially taller than the other inoculated plants, particularly compared to when these agents are used separately.

TABLE 3

| | | Height (cm) | | |
|---|---|---|---|---|
| Treatment | Rate | 5/26 | 6/21 | 7/10 |
| Non-inoculated control | — | 12.8 a | 36.4 ab | 38.0 a |
| Inoculated control | — | 13.0 a | 26.6 b | 22.5 c |
| T22 | 4 oz/100 gal | 13.0 a | 23.3 c | 30.4 b |
| G41 | 8 oz/100 gal | 13.7 a | 31.9 b | 32.6 b |
| T22 + G41 | 4 oz/100 gal + 8 oz/100 gal | 13.4 a | 36.2 ab | 41.6 a |
| Mefenoxam | 1 oz/100 gal | 13.8 a | 39.7 a | 39.8 a |
| LSD (P = 0.05) | | 1.97 | 2.74 | 2.19 |
| Standard Deviation | | 2.20 | 3.05 | 2.46 |
| CV | | 16.1 | 27.5 | 17.9 |

Mean values followed by different letters are significantly different (P = 0.05, Student-Newman-Keuls). Each value is a mean of 10 replicates.

As set forth in Table 4, the root and shoot weights of boxwoods significantly improved when treated with the combination of T22 and G41, particularly compared to when these agents are used separately.

TABLE 4

| Treatment | Rate | Fresh Shoot Weight(g) | | Dry Root Weight(g) | |
|---|---|---|---|---|---|
| | | 6/21 | 7/10 | 6/21 | 7/10 |
| Non-inoculated control | — | 71.6 a | 99.5 a | 13.5 a | 31.8 a |
| Inoculated control | — | 29.7 b | 35.3 d | 2.4 c | 9.1 d |
| T22 | 4 oz/100 gal | 39.1 b | 69.8 c | 8.1 b | 14.3 c |
| G41 | 8 oz/100 gal | 34.7 b | 75.5 bc | 9.3 b | 15.5 c |
| T22 + G41 | 4 oz/100 gal + 8 oz/100 gal | 84.0 a | 93.9 ab | 13.6 a | 29.4 a |
| Mefenoxam | 1 oz/100 gal | 86.2 a | 108.3 a | 16.7 a | 30.1 a |
| LSD (P = 0.05) | | 12.4 | 16.5 | 2.7 | 3.6 |
| Standard Deviation | | 9.6 | 12.7 | 2.2 | 2.8 |
| CV | | 17.8 | 15.5 | 19.8 | 12.8 |

Mean values followed by different letters are significantly different (P = 0.05, Student-Newman-Keuls). For each evaluation date, each value is a mean of 5 replicates.

Example 2—Treatment of Boxwoods Challenged with *Phytophthora cinnamomi*

This example gives an illustration of the efficacy and synergy of a composition according to the present invention for controlling *Phytophthora cinnamomi* on boxwood plants.

Boxwoods were subjected to the spray treatments set forth in Table 5. Except for the non-inoculated controls, each plant was treated with *P. cinnamomi* inoculum to induce disease. The methodology for this test was identical to that described in Example 1.

TABLE 5

| Treatment | Rate |
|---|---|
| 1. Non-Inoculated Control | — |
| 2. Inoculated Control | — |
| 3. G41 (*Trichoderma virens*) | 4 oz/100 gal |
| 4. G41 + T22 | 4 oz + 4 oz/100 gal |
| 5. Mefenoxam | 1 oz/100 gal |

Marketability results are set forth in Table 6. The combined treatment of T22 and G41 prevented the plants from developing disease symptoms and marketability remained high over time, particularly when compared to these treatments administered separately.

TABLE 6

| Treatment | Rate | Marketability: 1(dead)-5(excellent) Scale | | |
|---|---|---|---|---|
| | | Nov. 21, 2004 | Dec. 12, 2004 | Jan. 13, 2005 |
| Non-inoculated control | — | 5.0 a | 4.8 a | 4.9 a |
| Inoculated control | — | 5.0 a | 2.3 d | 1.8 e |
| G41 | 4 oz/100 gal | 5.0 a | 3.2 c | 3.0 d |
| G41 + T22 | 4 oz + 4 oz/100 gal | 5.0 a | 4.5 a | 4.5 ab |
| Mefenoxam | 1 oz/100 gal | 5.0 a | 4.6 a | 4.7 ab |
| LSD (P = 0.05) | | 0.00 | 0.46 | 0.56 |
| Standard Deviation | | 0.00 | 0.52 | 0.63 |
| CV | | 0.00 | 12.94 | 16.24 |

Mean values followed by different letters are significantly different (P = 0.05, Student-Newman-Keuls). Each value is a mean of 10 replicates.

Plants height results are shown in Table 7. Boxwoods subjected to the combined treatment of T22 and G41 were substantially taller than the other plants, particularly compared to when these agents are used separately.

TABLE 7

| Treatment | Rate | Height (cm) | | |
|---|---|---|---|---|
| | | Nov. 21, 2004 | Dec. 12, 2004 | Jan. 13, 2005 |
| Non-inoculated control | — | 12.9 ab | 37.4 a | 40.5 a |
| Inoculated control | — | 14.5 a | 28.2 d | 23.9 e |
| G41 | 4 oz/100 gal | 12.9 ab | 30.1 cd | 29.5 d |
| G41 + T22 | 4 oz + 4 oz/100 gal | 11.6 b | 34.2 ab | 37.7 ab |
| Mefenoxam | 1 oz/100 gal | 13.3 ab | 34.6 ab | 36.7 ab |
| LSD (P = 0.05) | | 1.39 | 3.61 | 3.26 |
| Standard Deviation | | 1.56 | 4.03 | 3.64 |
| CV | | 11.7 | 12.2 | 10.7 |

Mean values followed by different letters are significantly different (P = 0.05, Student-Newman-Keuls). Each value is a mean of 10 replicates.

As set forth in Table 8, the root and shoot weights of boxwoods were significantly improved when treated with the combination of T22 and G41. Plants treated with G41 alone had root and shoot weights that were significantly lower.

TABLE 8

| Treatment | Rate | Fresh Shoot Weight (g) | | Dry Root Weight (g) | |
|---|---|---|---|---|---|
| | | 12/12 | 1/13 | 12/12 | 1/13 |
| Non-inoculated control | — | 65.8 a | 87.2 a | 78.9 a | 104.2 a |
| Inoculated control | — | 30.9 c | 33.7 c | 28.7 d | 28.1 d |
| G41 | 4 oz/100 gal | 34.4 c | 39.6 c | 26.4 d | 33.5 cd |
| G41 + T22 | 4 oz + 4 oz/100 gal | 59.8 ab | 76.5 a | 70.7ab | 91.1 ab |
| Mefenoxam | 1 oz/100 gal | 64.8 a | 81.6 a | 76.4 a | 96.0 ab |
| LSD (P = 0.05) | | 13.6 | 14.6 | 13.1 | 15.3 |
| Standard Deviation | | 10.5 | 11.3 | 10.1 | 11.8 |
| CV | | 20.9 | 17.4 | 17.3 | 16.4 |

Mean values followed by different letters are significantly different (P = 0.05, Student-Newman-Keuls).
For each evaluation date, each value is a mean of 5 replicates.

Example 3—Treatment of Azaleas Challenged with *Phytophthora nicotianae*

This example gives an illustration of the efficacy and synergy of a composition according to the present invention for controlling *Phytophthora nicotianae* on azalea plants.

Azalea, *Rhododendron obtusum*, var. 'Pink Happy Days' plants were subjected to the spray treatments set forth in Table 9. Except for the non-inoculated controls, each plant was treated with *P. nicotianae* inoculum to induce disease. The methodology for this test was identical to that described in Example 1.

TABLE 9

| Treatment | Rate |
|---|---|
| 1. Non-Inoculated Control | — |
| 2. Inoculated Control | — |
| 3. G41 (*Trichoderma virens*) | 4 oz/100 gal |
| 4. G41 + T22 | 4 oz + 4 oz/100 gal |
| 5. Mefenoxam | 1 oz/100 gal |

Marketability results are set forth in Table 10. Marketability was maintained over the course of the experiment in plants treated with the combination of T22 and G41 biocontrol agents; protection from disease symptoms was equal to that of the chemical standard.

TABLE 10

| | | Marketability: 1(dead)-5(excellent) Scale | | |
|---|---|---|---|---|
| Treatment | Rate | Nov. 25, 2004 | Dec. 17, 2004 | Jan. 6, 2005 |
| Non-inoculated control | — | 5 a | 4.9 a | 4.8 a |
| Inoculated control | — | 5 a | 2.6 c | 1.7 d |
| G41 | 4 oz/100 gal | 5 a | 3.0 c | 2.6 c |
| G41 + T22 | 4 oz + 4 oz/100 gal | 5 a | 4.4 ab | 4.2 ab |
| Mefenoxam | 1 oz/100 gal | 5 a | 4.4 ab | 4.4 ab |
| LSD (P = 0.05) | | 0.0 | 0.63 | 0.60 |
| Standard Deviation | | 0.0 | 0.70 | 0.67 |
| CV | | 0.0 | 17.7 | 18.1 |

Mean values followed by different letters are significantly different (P = 0.05, Student-Newman-Keuls).
Each value is a mean of 10 replicates.

The results of the height evaluations are set forth in Table 11. Plants treated with the combination of T22 and G41 were significantly taller than plants treated with G41 alone, and equal to the height of plants treated with the chemical standard.

TABLE 11

| | | Height (cm) | | |
|---|---|---|---|---|
| Treatment | Rate | Nov. 25, 2004 | Dec. 17, 2004 | Jan. 6, 2005 |
| Non-inoculated control | — | 13.8 a | 29.4 a | 38.7 a |
| Inoculated control | — | 14.1 a | 13.5 e | 11.5 c |
| G41 | 4 oz/100 gal | 14.2 a | 20.5 d | 25.8 d |
| G41 + T22 | 4 oz + 4 oz/100 gal | 11.7 a | 24.1 bcd | 32.9 bc |
| Mefenoxam | 1 oz/100 gal | 13.7 a | 27.5 ab | 35.5 ab |
| LSD (P = 0.05) | | 1.18 | 2.89 | 4.07 |
| Standard Deviation | | 1.32 | 3.23 | 4.55 |
| CV | | 9.61 | 13.7 | 15.2 |

Mean values followed by different letters are significantly different (P = 0.05, Student-Newman-Keuls).
Each value is a mean of 10 replicates.

The fresh shoot weight and the dry shoot weight results are set forth in Table 12. Shoot and root weights were significantly higher in plants treated with the combination of G41 and T22, than in plants treated with G41 alone.

TABLE 12

| | | Fresh Shoot Weight (g) | | Dry Root Weight (g) | |
|---|---|---|---|---|---|
| Treatment | Rate | 6/21 | 7/10 | 6/21 | 7/10 |
| Non-inoculated control | — | 52.8 a | 78.2 a | 45.5 a | 60.7 a |
| Inoculated control | — | 21.9 d | 23.5 f | 21.3 d | 12.1 e |
| G41 | 4 oz/100 gal | 33.8 c | 41.2 e | 25.2 cd | 33.1 d |
| G41 + T22 | 4 oz + 4 oz/100 gal | 45.2 ab | 54.2 d | 31.3 bc | 44.8 c |
| Mefenoxam | 1 oz/100 gal | 49.0 ab | 70.3 ab | 44.2 a | 55.5 ab |
| LSD (P = 0.05) | | 6.9 | 8.62 | 6.31 | 7.73 |
| Standard Deviation | | 5.34 | 6.67 | 4.88 | 5.99 |
| CV | | 12.7 | 12.6 | 14.6 | 14.0 |

Mean values followed by different letters are significantly different (P = 0.05, Student-Newman-Keuls).
For each evaluation date, each value is a mean of 5 replicates.

Example 4—Treatment of Tomatoes Challenged with *Fusarium oxysporum*

This example gives an illustration of the efficacy and synergy of a composition according to the present invention for controlling *Fusarium oxysporum* f. sp. *lycopersici* on tomato plants.

Tomato, *Lycopersicon esculentum*, var *esculentum* 'Beefsteak', seedlings were subjected to the soil drench treatments set forth in Table 13. Except for the non-inoculated controls, each plant was treated with inoculum of the pathogen *F. oxysporum* f. sp. *lycopersici* to induce disease.

Tomatoes were started in 128-cell flats from seeds in a general purpose, peat-based growing medium. Plants were watered with a 100 ppm solution of 20-20-20 water-soluble plant food (Jack's Classic). At 4-5 days after planting, the seedlings were drenched with the biological materials mixed in water. Seedlings not receiving treatments at this time were treated only with the blank formulation (without *Trichoderma*).

Inoculum of *F. oxysporum* was grown on sterilized rice grains for 7 days at 24-26° C. The rice was uniformly blended into growing medium at a rate of 5% (weight: weight). Seven day old tomato seedlings were transplanted into 4 inch pots that contained the pathogen inoculum on rice. A set of untreated control seedlings were transplanted into pots containing the growing medium plus uninoculated rice. A set of seedlings was drenched with the label rate of mefenoxam to serve as the chemical fungicide standard and a set of treated control seedlings was transplanted into medium containing the pathogen.

Plants were maintained in a growing room at 20-24° C. under a 12 hour light: dark cycle. Plants were watered with a nutrient solution as described above. At 28 DAI, the experiment was terminated, and each plant was cut into two portions: root (below ground) and shoot (above ground). The material was dried in an oven at 60° C. until completely dry (approximately 24 hours) and the weights recorded. Data were subjected to a one-way ANOVA after Bonferroni correction. Significant differences between treatment means were determined using Tukey's HSD test at P=0.05.

TABLE 13

| Treatment | Concentration |
| --- | --- |
| 1. Non-Inoculated Control | — |
| 2. Inoculated Control | — |
| 3. T22 (*Trichoderma harzianum*) | 4 oz/100 gal |
| 4. G41 (*Trichoderma virens*) | 4 oz/100 gal |
| 5. T22 + G41 | 4 oz + 4 oz/100 gal |
| 6. Mefenoxam | 1 oz/100 gal |

As set forth in Table 14, the root and shoot weights of tomatoes significantly improved when treated with the combination of T22 and G41, particularly compared to when these agents are used separately and in comparison to the chemical standard.

TABLE 14

| Treatment | Rate | Dry Shoot Weight (g) | Dry Root Weight (g) |
| --- | --- | --- | --- |
| Non-inoculated control | — | 1.33 ab | 0.17 b |
| Inoculated control | — | 0.60 c | 0.06 c |
| T22 | 4 oz/100 gal | 0.91 bc | 0.16 b |
| G41 | 4 oz/100 gal | 0.87 c | 0.12 bc |
| T22 + G41 | 4 oz/100 gal + 4 oz/100 gal | 1.50 a | 0.30 a |
| Mefenoxam | 1 oz/100 gal | 0.90 bc | 0.12 bc |
| Tukey's HSD (P = 0.05) | | 0.44 | 0.10 |

Mean values in each column followed by the same letter are not significantly different according to Tukey's HSD (P = 0.05)
For each treatment, each value is a mean of 28 replicates (plants).

Example 5—Treatment of Tomatoes Challenged with *Pythium irregulare*

This example gives an illustration of the efficacy and synergy of a composition according to the present invention for controlling *Pythium irregulare* on tomato plants.

Tomato, *Lycopersicon esculentum*, var *esculentum* 'Beefsteak', seedlings were subjected to the soil drench treatments set forth in Table 13. Except for the non-inoculated controls, each plant was treated with inoculum of the pathogen *Pythium irregulare* to induce disease.

Tomato seedlings were grown and treated as described above in Example 2. Sterile rice was inoculated with a suspension of *P. irregulare* at the rate of 1 colonized PDA Petri plate/1 liter of sterile water. Rice was incubated for 24 hours at 24-26° C. Infested rice was uniformly blended into the growing medium at a rate of 5% (weight: weight).

Tomato seedlings were transplanted into 4 inch pots that contained the pathogen inoculum on rice. A set of untreated control seedlings were transplanted into pots containing the growing medium plus rice, but no pathogen. A set of seedlings was drenched with the label rate of mefenoxam to serve as the chemical standard and a set of treated control seedlings was transplanted into medium containing the pathogen.

Plants were maintained in a growing room at 20-24° C. under a 12 hour light: dark cycle. Plants were watered with a nutrient solution as described above. At 21 DAI, the experiment was terminated, and the plants were each separated into two parts: root (below ground) and shoot (above ground). The material was dried in an oven until completely dry (approximately 24 hours) and the weights recorded.

As set forth in Table 15, the root and shoot weights of tomato plants significantly improved when treated with the combination of T22 and G41, particularly compared to when these agents are used separately and in comparison to the chemical standard.

TABLE 15

| Treatment | Rate | Dry Shoot Weight (g) | Dry Root Weight (g) |
| --- | --- | --- | --- |
| Non-inoculated control | — | 0.52 a | 0.07 a |
| Inoculated control | — | 0.37 bcd | 0.06 ab |
| T22 | 4 oz/100 gal | 0.32 cd | 0.05 b |
| G41 | 4 oz/100 gal | 0.39 bc | 0.06 ab |
| T22 + G41 | 4 oz/100 gal + 4 oz/100 gal | 0.43 ab | 0.07 a |
| Mefenoxam | 1 oz/100 gal | 0.28 d | 0.04 c |
| Tukey's HSD (P = 0.05) | | 0.10 | 0.02 |

Mean values in each column followed by the same letter are not significantly different according to Tukey's HSD (P = 0.05)
For each treatment, each value is a mean of 28 replicates (plants).

Example 6—Treatment of Cucumber Seeds to Protect Against *Pythium aphanidermatum*

This example gives an illustration of the efficacy and synergy of a composition according to the present invention applied as a seed coating for controlling *Pythium aphanidermatum* on cucumber seedlings.

Cucumber, *Cucumis sativus*, var Marketmore 76 seeds were coated with *T. harzianum* and/or *T. virens*, or mefenoxam as described by Pill et al. (Pill et. al., *Scientia Horticulturae* 121:54-62 (2009), which is hereby incorporated by reference in its entirety). Seeds were planted into flats with or without *P. aphanidermatum* inoculum. The experiment was conducted in a greenhouse with natural lighting and temperature settings of 25/22° C. (day/night). The numbers of seedlings emerged were recorded daily until there was no increase for two consecutive days. Diseased plants were recorded as either pre- (no seedling emergence) or post-emergent (shoot lodging). These data were subjected to analysis of variance and means separated by LSD test at P=0.05.

As set forth in Table 16, the percent damping off-both pre-emergence and total—was significantly reduced when the seeds were treated with the combination of T22 and G41, particularly compared to when these agents are used separately, and in comparison to the chemical standard.

TABLE 16

| Seed Treatment | Percent Damping-Off | |
|---|---|---|
| | Pre-emergence | Total |
| None | 19.4 a | 33.3 a |
| T22 | 7.0 b | 15.9 b |
| G41 | 2.3 bc | 9.8 c |
| T22 + G41 | 0 c | 0 d |
| Mefenoxam | 4.6 bc | 9.3 c |

Mean values in each column followed by the same letter are not significantly different according to LSD (P = 0.05)

Example 7—Treatment of Tomatoes Challenged with *Rhizoctonia solani*

This example gives an illustration of the efficacy and synergy of a composition according to the present invention for controlling *Rhizoctonia solani* on tomato plants.

Tomato, *Lycopersicon esculentum*, var *esculentum* 'Beefsteak', seedlings were subjected to the soil drench treatments set forth in Table 13, except that there were no untreated control plants. Except for the non-inoculated controls, each plant was treated with inoculum of the pathogen *R. solani* to induce disease.

Tomato seedlings were grown and treated as described above in Example 2. Sterile rice was inoculated with agar plugs from PDA Petri plates containing growing colonies of *R. solani* at a rate of one colonized PDA plate/500 g rice. Rice was incubated for 10 days at 24-26° C. Infested rice was uniformly blended into the growing medium at a rate of 5% (weight: weight).

Tomato seedlings were transplanted into 4 inch pots that contained the pathogen inoculum on rice. The untreated check plants became contaminated with an unknown disease and were not included in the analysis. A set of seedlings was drenched with the label rate of mefenoxam to serve as the chemical standard and a set of treated control seedlings was transplanted into medium containing the pathogen.

Plants were maintained in a growing room at 20-24° C. under a 12 hour light: dark cycle. Plants were watered with a nutrient solution as described above. At 23 DAI, the experiment was terminated, and the plants were each separated into two parts: root (below ground) and shoot (above ground). The material was dried in an oven at 60° C. until completely dry (approximately 24 hours) and the weights recorded. Data were analyzed as described in Example 2, above.

As set forth in Table 17, the root and shoot weights of tomato plants significantly improved when treated with the combination of T22 and G41, particularly compared to when these agents are used separately and in comparison to the chemical standard.

TABLE 17

| Treatment | Rate | Dry Shoot Weight (g) | Dry Root Weight (g) |
|---|---|---|---|
| Inoculated control | — | 0.52 bc | 0.06 b |
| T22 | 4 oz/100 gal | 0.67 b | 0.09 ab |
| G41 | 4 oz/100 gal | 0.61 b | 0.08 ab |
| T22 + G41 | 4 oz/100 gal + 4 oz/100 gal | 0.86 a | 0.11 a |
| Mefenoxam | 1 oz/100 gal | 0.42 c | 0.06 b |
| Tukey's HSD (P = 0.05) | | 0.10 | 0.02 |

Mean values in each column followed by the same letter are not significantly different according to Tukey's HSD (P = 0.05)
For each treatment, each value is a mean of 28 replicates (plants).

Example 8—Demonstration of the Significance of Rhizosphere Competency to Synergy Part I. Evaluating Relative Rhizosphere Competency
Evaluating the Relative Rhizosphere Competency of T22 and G41

Rhizosphere competency was measure in corn seedlings using the methodology described (Chao et. al. *Phytopathology* 76:60-65 (1986), which is hereby incorporated by reference in its entirety). Corn seedlings treated with T22 and G41 were planted in aluminum foil tubes containing sterile soil. After 10 days, the tubes were carefully unrolled; the plant roots were cut into 1.0 inch segments from the tip to the crown of the plant. Each segment was assayed for the relative amount of each *Trichoderma* strain.

Figure 1:
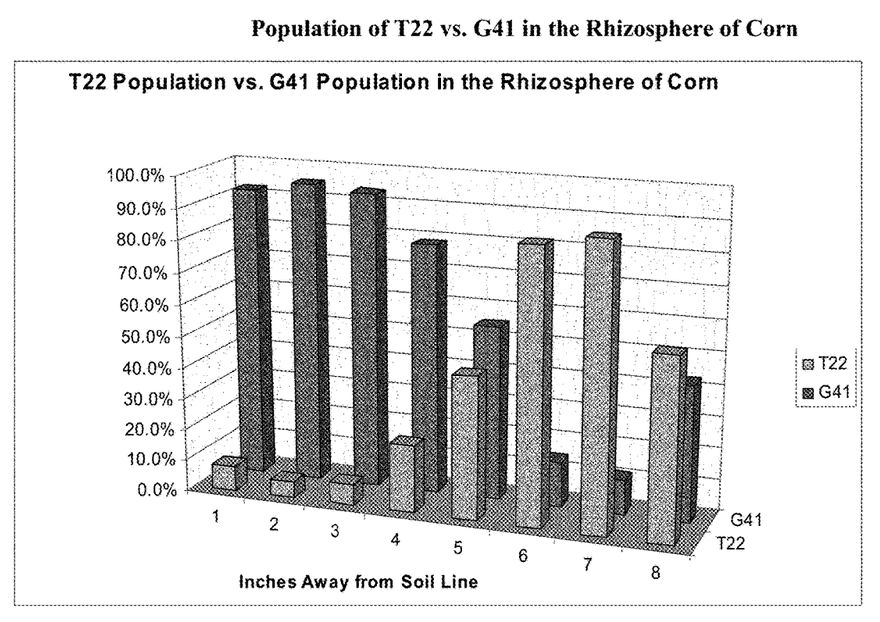
FIG. 1 is a plot of the population of T22 versus G41 in the rhizosphere of corn.

FIG. 1 shows the relative populations of T22 and G41 (as percentages of the total *Trichoderma* population) found in 1 inch root segments of treated corn. G41 was found to inhabit mostly the top 4-5 inches directly below the soil line, while T22 was found to inhabit the roots in the bottom 6-8 inches. This indicates that T22 populations grow along the root tip, whereas G41 populations primarily inhabit the upper portions of the root. According to Sivan and Harman (Sivan and Harman, *J. Gen. Microbiol.* 137: 23-29 (1991), which is hereby incorporated by reference in its entirety) the ability of T22 to grow along the root tip makes it rhizosphere competent, as compared to G41, which did not grow along the lower portions of the root and root tip. By inhabiting different portions of the root, T22 and G41 populations avoid direct competition for space and nutrients.

Part II. Significance of Rhizosphere Competency to Biocontrol

In order to demonstrate the significance of rhizosphere competency to the synergy and enhanced biocontrol activity when two strains of *Trichoderma* are combined, tests were conducted in vivo in plants challenged by pathogens. In Experiment 1, the efficacy of a combination of T22 with an alternate strain of *T. virens*, strain G21, was evaluated. In Experiment 2, the efficacy of a combination of a non-rhizosphere competent strain of *T. harzianum*, strain T12 and G41, was evaluated.

Experiment 1. Demonstrating Synergy with a Combination of T22 and G21

Cucumber, *Cucumis sativus* var Marketmore 76, seedlings were subjected to the soil drench treatments set forth in Table 18. Except for the non-inoculated controls, each plant was treated with inoculum of the pathogen *Pythium irregulare* to induce disease.

Seedlings were grown and treated as described in Example 4. Sterile rice was inoculated with a suspension of

*P. irregulare* at the rate of one colonized PDA Petri plate/1 liter of sterile water. Rice was incubated for 24 hours at 24-26° C. Infested rice was uniformly blended into the growing medium at a rate of 5% (weight: weight).

Cucumber seedlings were transplanted into 4 inch pots that contained the pathogen inoculum on rice. A set of untreated control seedlings were transplanted into pots containing the growing medium plus rice, but no pathogen. A set of seedlings was drenched with the label rate of mefenoxam to serve as the chemical standard and a set of treated control seedlings was transplanted into medium containing the pathogen.

Plants were maintained in a growing room at 20-24° C. under a 12 hour light: dark cycle. At 28 DAI, the experiment was terminated, and the plants were each separated into two parts: root (below ground) and shoot (above ground). The material was dried in an oven at 60° C. until completely dry (approximately 24 hours) and the weights recorded. Data were analyzed as described in Example 4.

TABLE 18

| Treatment | Rate |
|---|---|
| 1. Non-Inoculated Control | — |
| 2. Inoculated Control | — |
| 3. T22 (*Trichoderma harzianum*) | 4 oz/100 gal |
| 4. G21 (*Trichoderma virens*) | 4 oz/100 gal |
| 5. T22 + G21 | 4 oz + 4 oz/100 gal |
| 6. Mefenoxam | 1 oz/100 gal |

As set forth in Table 19, the root and shoot weights of cucumber plants significantly improved when treated with the combination of T22 and G21, particularly compared to using these agents separately and in comparison to the chemical standard. These data show that when T22, a rhizosphere competent strain of *Trichoderma harzianum*, is combined with an alternate strain of *T. virens*, a synergistic effect is still observed and efficacy is enhanced.

TABLE 19

| Treatment | Rate | Dry Shoot Weight (g) | Dry Root Weight (g) |
|---|---|---|---|
| Non-inoculated control | — | 0.84 a | 0.14 a |
| Inoculated control | — | 0.37 c | 0.07 c |
| T22 | 4 oz/100 gal | 0.58 b | 0.10 abc |
| G21 | 4 oz/100 gal | 0.48 bc | 0.08 c |
| T22 + G21 | 4 oz/100 gal + 4 oz/100 gal | 0.88 a | 0.13 ab |
| Mefenoxam | 1 oz/100 gal | 0.66 ab | 0.10 abc |
| Tukey's HSD (P = 0.05) | | 0.19 | 0.05 |

Mean values in each column followed by the same letter are not significantly different according to Tukey's HSD (P = 0.05)
For each treatment, each value is a mean of 14 replicates (plants).

Experiment 2. Demonstrating a Loss of Synergy with a Combination of T12 and G41

It has been demonstrated that *Trichoderma harzianum* strain T12 (ATCC 20737) does not posess the ability to grow along the root tip. Thus, it is not a rhizosphere competent strain (Chao et al., "Colonization of the Rhizosphere by Biological Control Agents Applied to Seeds," *Phytopathology* 76:60-65 (1986), which is hereby incorporated by reference in its entirety). This experiment was conducted to demonstrate the loss of synergy when a non-rhizosphere competent strain of *T harzianum* is used for disease control.

Tomato, *Lycopersicon esculentum*, var *esculentum* 'Beefsteak', seedlings were subjected to the soil drench treatments set forth in Table 20. Except for the non-inoculated controls, each plant was treated with inoculum of the pathogen *Fusarium oxysporum* f. sp. *lycopersici* to induce disease. Experimental procedures and data analysis were identical to those described in Example 4.

TABLE 20

| Treatment | Rate |
|---|---|
| 1. Non-Inoculated Control | — |
| 2. Inoculated Control | — |
| 3. T12 (*Trichoderma harzianum*) | 4 oz/100 gal |
| 4. G41 (*Trichoderma virens*) | 4 oz/100 gal |
| 5. T12 + G41 | 4 oz + 4 oz/100 gal |
| 6. Mefenoxam | 1 oz/100 gal |

As set forth in Table 21, the root and shoot weights of tomato plants were not significantly different in the combination treatment of T12+G41 compared to using these agents separately and compared to the chemical standard. These data show that when T12, a non-rhizosphere competent strain of *Trichoderma harzianum*, is combined with a *Trichoderma virens* strain, no synergistic effect is observed. This may be due to the inability of T12 to grow along the advancing roots and protect the vulnerable root tips from attack by pathogens. Further, the T12 may compete for nutrients and space with G41 in the upper portions of the root zone.

TABLE 21

| Treatment | Rate | Dry Shoot Weight (g) | Dry Root Weight (g) |
|---|---|---|---|
| Non-inoculated control | — | 0.70 a | 0.05 a |
| Inoculated control | — | 0.39 bc | 0.03 b |
| T12 | 4 oz/100 gal | 0.52 ab | 0.05 a |
| G41 | 4 oz/100 gal | 0.54 ab | 0.05 a |
| T12 + G41 | 4 oz/100 gal + 4 oz/100 gal | 0.50 ab | 0.05 a |
| Mefenoxam | 1 oz/100 gal | 0.17 c | 0.03 b |
| Tukey's HSD (P = 0.05) | | 0.23 | 0.02 |

Mean values in each column followed by the same letter are not significantly different according to Tukey's HSD (P = 0.05)
For each treatment, each value is a mean of 14 replicates (plants).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A method of controlling plant diseases mediated by *Phytophthora, Pythium, Fusarium, Rhizoctonia, Thielaviopsis*, and/or *Sclerotium* species, said method comprising:
   a) a providing growing plants in an environment susceptible to a plant disease mediated by *Phytophthora, Pythium, Fusarium, Rhizoctonia, Thielaviopsis*, and/or *Sclerotium* species;
   b) providing a culture of a rhizosphere competent *Trichoderma harzianum* strain;
   c) providing a culture of a *Trichoderma virens* strain; and
   d) applying effective amounts of the cultures of the *Trichoderma harzianum* strain and of the *Trichoderma virens* strain to the growing plants to treat plant diseases mediated by *Phytophthora, Pythium, Fusarium, Rhizoctonia, Sclerotium*, and/or *Thielaviopsis* species, wherein either the *T. harzianum* strain is T22 or the *T. virens* strain is G41.

2. The method of claim 1, wherein the plant disease is mediated by a *Phytophthora* species selected from the group consisting of *Phytophthora cactorum, Phytophthora cinnamomi, Phytophthora citricola, Phytophthora citrophthora, Phytophthora cryptogea, Phytophthora drecshsleri, Phytophthora infestans*, and *Phytophthora nicotianae*.

3. The method of claim 1, wherein the plant disease is mediated by a *Pythium* species selected from the group consisting of *Pythium aphanidermatum, Pythium irregulare*, and *Pythium ultimum*.

4. The method of claim 1, wherein the plant disease is mediated by *Fusarium oxysporum*.

5. The method of claim 1, wherein the plant disease is mediated by *Rhizoctonia solani*.

6. The method of claim 1, wherein the plant disease is mediated by *Thielaviopsis basicola*.

7. The method of claim 1, wherein the plant disease is mediated by *Sclerotium rolfsii*.

8. The method of claim 1, wherein the growing plant is selected from the group consisting of flowers, bedding plants, ornamentals, fruiting vegetables, hydroponic crops, leafy vegetables and cole crops, pome fruit, deciduous trees, grapes, citrus, pine, stone fruit, tree nuts, grains, and grasses.

9. The method of claim 1, wherein said applying is carried out by broadcast application, liquid or dry in-furrow application, drenching of potted plants, direct incorporation into soils or greenhouse planting mixes, or application of granular formulations or granules.

10. The method of claim 1, wherein the rhizosphere competent *Trichoderma harzianum* strain and the *Trichoderma virens* strain are provided in the form of a biocontrol composition and said applying is carried out by applying the biocontrol composition.

11. The method of claim 10, wherein the biocontrol composition further comprises a carrier.

12. The method of claim 11, wherein the carrier is selected from the group consisting of water, aqueous solutions, slurries, granules, and powders.

13. The method of claim 10, wherein the biocontrol composition further comprises an additive selected from the group consisting of fertilizer, insecticide, fungicide, nematicide, and mixtures thereof.

14. The method of claim 1, wherein the *Trichoderma harzianum* strain is T22.

15. The method of claim 1, wherein the *Trichoderma virens* strain is G41.

16. The method of claim 1, wherein the *Trichoderma harzianum* strain is T22 and wherein the *Trichoderma virens* strain is G41.

* * * * *

UNITED STATES PATENT AND TRADEMARK OFFICE
CERTIFICATE OF CORRECTION

PATENT NO.        : 9,681,668 B2
APPLICATION NO.   : 14/610104
DATED             : June 20, 2017
INVENTOR(S)       : Martin, Jr. et al.

Page 1 of 1

It is certified that error appears in the above-identified patent and that said Letters Patent is hereby corrected as shown below:

In the Claims

Claim 1, at Column 20, Line 58, delete "a" after "a)" and before the word "providing".

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*